United States Patent [19]
Eadington et al.

[11] Patent Number: 5,969,240
[45] Date of Patent: Oct. 19, 1999

[54] METHODS FOR DETERMINING IRREDUCIBLE WATER RESISTIVITY AND ESTIMATING OIL WELL RESERVES

[75] Inventors: Peter John Eadington, East Ryde; Mark Lisk; Francis William Krieger, both of North Ryde, all of Australia

[73] Assignee: Commonwealth Scientific and Industrial Research Organisation, Campbell, Australia

[21] Appl. No.: 08/983,101

[22] PCT Filed: Aug. 12, 1996

[86] PCT No.: PCT/AU96/00505

§ 371 Date: Apr. 29, 1998

§ 102(e) Date: Apr. 29, 1998

[87] PCT Pub. No.: WO97/08540

PCT Pub. Date: Mar. 6, 1997

[30] Foreign Application Priority Data

Aug. 23, 1995 [AU] Australia .................... PN4971

[51] Int. Cl.$^6$ .......................... E21B 49/00; G01N 33/24; G01N 27/06
[52] U.S. Cl. .................. 73/152.09; 73/152.06; 436/31; 436/150
[58] Field of Search ............. 73/152.08, 152.09, 73/152.06, 866; 702/7, 11; 436/28, 31, 150; 324/323, 339, 376

[56] References Cited

U.S. PATENT DOCUMENTS

| | | |
|---|---|---|
| 2,583,284 | 1/1952 | Wyllie . |
| 2,617,296 | 11/1952 | Wisenbaker . |
| 3,207,615 | 9/1965 | Tinklepaugh . |
| 3,371,527 | 3/1968 | Moulin . |
| 3,770,378 | 11/1973 | Russell ................. 436/31 |
| 4,233,839 | 11/1980 | Coates ................ 73/152.08 |
| 4,752,882 | 6/1988 | Givens ................ 73/152.05 |
| 4,960,567 | 10/1990 | Smith ..................... 422/78 |
| 5,105,154 | 4/1992 | Givens ................. 324/376 |
| 5,126,939 | 6/1992 | Carpenter ............ 324/339 |
| 5,241,859 | 9/1993 | Smith ................. 73/53.01 |
| 5,395,768 | 3/1995 | Nery ..................... 436/31 |
| 5,861,750 | 1/1999 | Anderson et al. ........ 73/152.06 |

FOREIGN PATENT DOCUMENTS

| | | |
|---|---|---|
| 1125442 | 8/1968 | United Kingdom . |
| 2268274 | 1/1994 | United Kingdom . |

OTHER PUBLICATIONS

Asquith, George, Gibson, Charles, Basic Well Log Analysis for Geologists, The American Association of Petroleum Geologists, p. 102. Oct. 1982.

*Primary Examiner*—Hezron Williams
*Assistant Examiner*—Chad Soliz
*Attorney, Agent, or Firm*—Ladas & Parry

[57] ABSTRACT

A method for determining the resistivity of water in an oil well site that includes rock that is capable of water entrapment, includes the steps of:
(a) retrieving a sample of the rock;
(b) identifying any entrapped water in the sample; and
(c) determining the resistivity of the entrapped water. The so determined resistivity then enables oil reserves to be calculated in the well site.

12 Claims, 2 Drawing Sheets

METHODS FOR DETERMINING IRREDUCIBLE WATER RESISTIVITY AND ESTIMATING OIL WELL RESERVES

FIELD OF THE INVENTION

The present invention relates to a method for determining irreducible water resistivity in an oil well site and to methods for estimating oil reserves in the oil well site from calculated resistivity.

BACKGROUND ART

Oil well sites often occur in porous rock formations (eg. sub-sea formations) whereby oil and water (and often gas) are stored or retained in the pores of the rock (eg. between grains of granular rocks such as sandstone). Specifically, the water is retained in the pore spaces as a film between any oil and, for granular rocks, individual grains and has low mobility. This water is referred to in the art as "irreducible". In other words, it is held in the rock in the pore spaces through capillary forces and is not removed when oil is retrieved from the site.

It is known that an estimation of oil reserves in a rock site can be made if the amount of irreducible water can be determined. One technique for determining this amount is to calculate and/or measure the water's resistivity (ie. electrical resistivity) and from this the water saturation (and thence oil saturation) of the oil well can be determined. However, existing tests for determining irreducible water resistivity are highly prone to error.

For example, resistivity manual measurement techniques involve the retrieval of a granular rock sample and the direct measurement of resistivity on water extracted from the rock sample but such tests are effected by mud filtrate contamination (ie. mud filtrate is captured when the sample is retrieved and contaminates the irreducible water in the sample).

To overcome introduced inaccuracies, calculating methods have been evolved which are not effected by mud filtrate contamination. One preferred technique is referred to as the "sp method" (spontaneous potential log method) which is a calculative technique based upon the voltage effect between the drilling mud and the formation water in a porous rock. The sign of the voltage switches polarity depending on whether the drilling mud is more or less saline than the irreducible water. The SP method is, however, notoriously uncertain and is effected by clay minerals and other influences not related to salinity. It would be advantageous to provide a technique that is not effected by such variables.

SUMMARY OF THE INVENTION

The present invention provides a method for determining the resistivity of water in an oil well site that includes rock that is capable of water entrapment, including the steps of:

(a) retrieving a sample of the rock;
(b) identifying any entrapped water in the sample;
(c) determining the resistivity of the entrapped water.

Entrapped water is irreducible water which has been trapped intragranularly during, for example, formation of the rock or crystallisation of minerals within a rock. The method of the present invention can be employed for water that is entrapped as intracrystalline inclusions in "granular-type" rocks (eg. sandstone) within grains themselves of the rock. Alternatively, the method can be employed for other rocks in oil well sites (eg. carbonate type rocks) where the irreducible water is entrapped as intracrystalline inclusions in the rock so as to be permanently separated off from surrounding irreducible water.

Thus, the entrapped water is a pristine sample of surrounding irreducible water. The entrapped water is not affected during sampling as it is protected within the rock (eg. within the grain). In most cases the entrapped water is entrapped with oil and the entrapped water can thus be identified by firstly locating the entrapped oil.

In this specification, the terms "oil well" and "oil well site" include a site suspected of containing oil (eg. a site located during oil exploration).

Preferably, in step (c) the resistivity is determined from a determination of salinity of the entrapped water. A preferred method for determining salinity is:

(1) freezing the entrapped water in the sample;
(2) causing or allowing the frozen water to melt;
(3) observing the final melting temperature of the water; and
(4) calculating salinity from the observed final melting temperature.

Salinity S is preferably calculated in step (4) according to the formula:

$$S = (-1.76 T_{ice} - 0.041 T_{ice}^2 - 0.00037 T_{ice}^3) \times 10000 \qquad (1)$$

where $T_{ice}$ is the final melting temperature determined in step (3).

Once salinity has been calculated resistivity is preferably calculated according to the formula:

$$Rw_{FT} = 2330.9 \times (S^{-0.8995}) \times \frac{82}{1.8 \times FT(^\circ C.) + 39} \qquad (2)$$

where $Rw_{FT}$ is the resistivity of irreducible water at a reservoir (or formation) temperature, S is the salinity calculated in formula (1) and FT is the formation temperature in °C.

Thus, an accurate resistivity reading can be determined, and this can be used for estimating oil reserves in an oil well site.

Oil reserves can be estimated by the steps of:

(i) determining entrapped water resistivity in a method as defined above for the first aspect;
(ii) from the entrapped water resistivity determined in step (i), calculating the water saturation of the well site; and
(iii) from the calculated water saturation of step (ii), calculating the oil saturation of the well site to enable the estimation of site oil reserves to be made.

When the site is granular rock based, it is preferred that the rock is clean sandstone (i.e. sandstone that does not contain shale) and preferably in step (ii) water saturation is calculated according to the formula:

$$Sw = \left( \frac{a}{\phi^m} \times \frac{Rw}{Rt} \right)^{\frac{1}{n}} \qquad (3)$$

which is known as the Archie equation; (its variants may include a term to take account of sandstone containing shale). In equation (3):

Sw=water saturation of uninvaded zone of the site (i.e. that part of the oil well site not invaded by mud filtrate from drilling),
Rw=resistivity of formation water calculated in formula (2), Rt=true resistivity of the formation (ie. corrected for invasion), φ=the site porosity, a=the tortuosity factor, m=cementation exponent, and n=saturation exponent (which for sandstone varies from 1.8 to 2.5 but is normally equal to 2.0).

Preferably, in step (iii) oil saturation is calculated according to the formula:

$$So = 1 - Sw \quad (4)$$

where

So=oil saturation, and Sw is the water saturation calculated from formula (3);

and oil well reserves are then estimated according to the formula:

$$N_r = \frac{7758 \times DA \times h \times \phi \times So \times RF}{BOI} \quad (5)$$

where

Nr=volumetric recoverable oil reserves in stock tank barrels (STB),

DA=drainage area in acres, h=reservoir thickness in feet,

φ=porosity,

So=oil saturation (i.e. 1.0–Sw),

RF=recovery factor,

BOI=oil volume factor or reservoir barrels per stock tank barrel, and

GOR=gas oil ratio;

where $$BOI = 1.05 + 0.5 \times \left(\frac{GOR}{100}\right) \quad (6)$$

and $$GOR = \frac{\text{gas in cubic feet}}{\text{oil in barrels}} \quad (7)$$

In this manner, an estimation of oil reserves in the oil well site can be made based on an accurate resistivity reading.

The entrapped water can be trapped within rock grains as a three-phase inclusion comprising oil, water and gas. When entrapped water is located by locating entrapped oil, it is preferred that the entrapped oil is identified by irradiating the sample with violet and/or ultraviolet light, preferably of wavelengths less than 4000 Angstrom.

The techniques described above can be used to determine resistivity and estimate oil reserves when test drilling (ie. during exploration) or after commercial exploitation of an oil site has already commenced.

BRIEF DESCRIPTION OF THE DRAWINGS

Notwithstanding any other forms which may fall within the scope of the present invention, preferred forms of the invention will now be described, by way of example only, with reference to non-limiting examples and the accompanying drawings in which.

MODES FOR CARRYING OUT THE INVENTION

Figure 1:
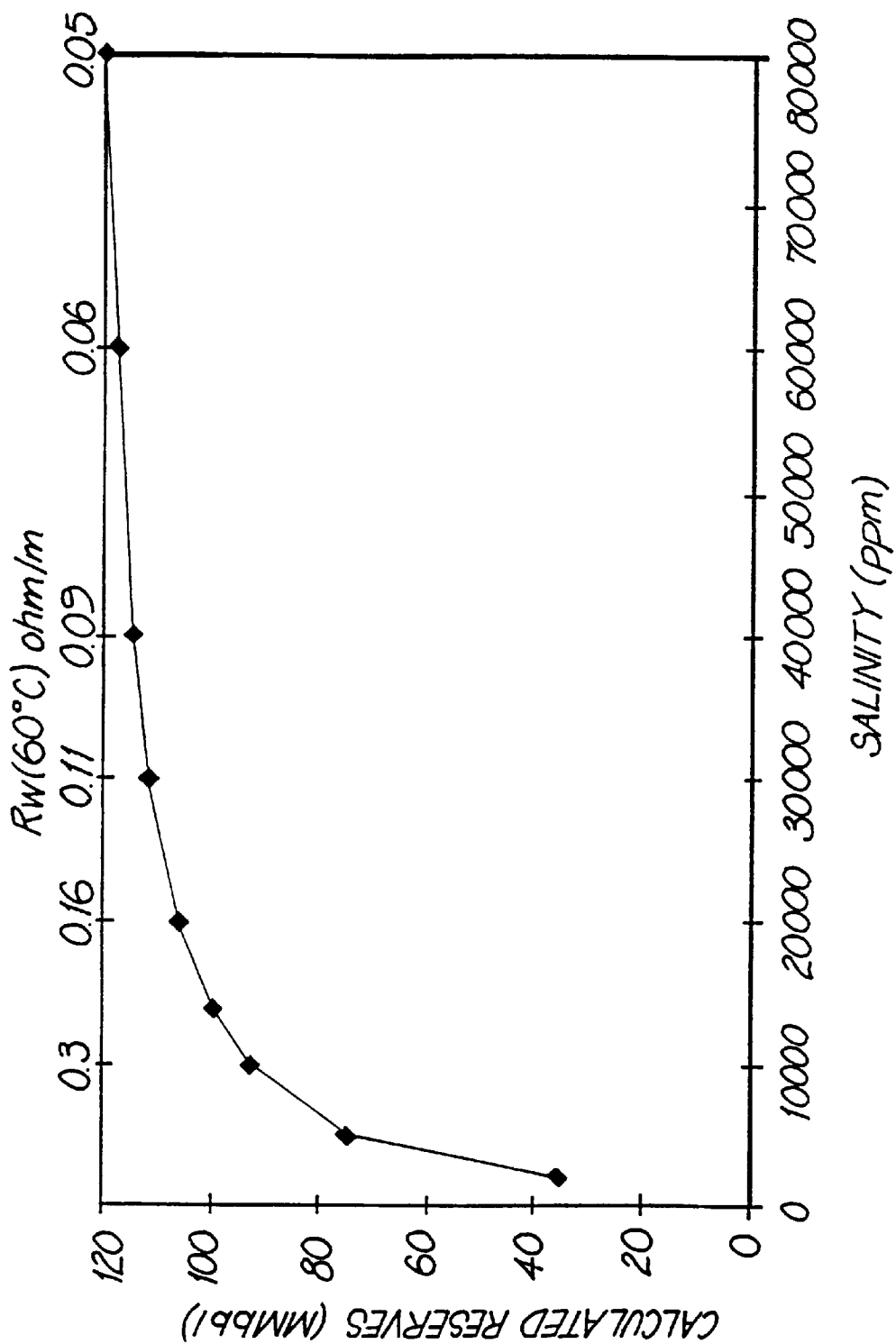
FIG. 1 is a graphical plot of the change of salinity/resistivity against calculated oil reserves.

The following examples focus on using preferred techniques according to the present invention on granular-based clastic rock samples, but it should be appreciated that the techniques are equally applicable to rocks that are not, as such, granular clastic but that still entrap irreducible water (eg. enclosed within rock grains in granular massive rock— for example, in carbonate based rocks). In the latter case, parameters in the calculations are appropriately altered (as would be understood by the skilled person in the art).

Natural fluid inclusions in granular rock samples, typically fluid inclusions containing oil, water and gas (referred to herein as "three-phase inclusions"), were used to determine the resistivity of irreducible water in an oil column (or well). Resistivity is related to ionic properties of aqueous solutions and correlates with salinity.

In preferred methods, resistivity (Ωm) was determined by referring an ice melting temperature (°C.) measured on the aqueous part of the three-phase inclusion to experimental curves for salinity (ppm) and resistivity (Ωm).

The preferred methods recognised that oil saturation in a reservoir (which is a fundamental parameter in the calculation of oil reserves) cannot be determined directly, but rather is estimated as the difference between the porosity in the rock and the amount (or saturation) of irreducible water.

Previously, water saturation was conventionally determined from the electrical resistivity within the formation, measured by electrodes in a wireline resistivity tool, however, this technique is critically dependent on a knowledge of the resistivity of the irreducible water.

Also this technique has many shortcomings because it is difficult to obtain a sample of irreducible water because of its low mobility and because water samples taken from a drill hole mix with and are contaminated by water and the drill mud that fills the hole.

Another existing method measured the resistivity of water underlying an oil well (e.g. held in granular rock, such as sandstone, beneath the oil well). Such zones are referred to as "aquifers" and the technique assumed that aquifer resistivity equated with irreducible water resistivity. However, the water in aquifers is often mobile and may differ considerably in resistivity from irreducible water in the oil zone.

By determining resistivities of entrapped water such as intra-granular water, inaccuracies introduced through contamination, dilution, etc., were avoided, because the water is inaccessible to such contamination, dilution, etc.

EXAMPLES

Example 1

Samples of reservoir rock from an oil zone were retrieved during drilling of the oil well. Samples included rotary core, cuttings, sidewall core and rotary sidewall core. The samples were cut, ground and polished and then prepared as a thin section (eg. 0.08 mm thick) on a glass slide with polished upper and lower surfaces and no cover glass. The core samples were impregnated with epoxy prior to preparation while cutting samples were dispersed in epoxy.

Three-phase fluid inclusions were then identified under a microscope by irradiating the sample with ultraviolet light. The three-phase inclusions were identified when the hydrocarbon fluid fraction (ie. the oil fraction) absorbed the ultraviolet light (typically of a wavelength less than 4000 Angstrom) and fluoresced (ie. re-emitted this light)— typically at wavelengths greater than about 4200 Angstrom.

The microscope was also provided with a heating/freezing stage. This stage was used to determine ice melting temperature. Specifically, once a sample had been identified as being three-phase, it was frozen on the heating/freezing stage and then allowed to thaw. The ice melting temperature was then recorded. By observing the point at which the inclusion no longer contained ice, and recording that temperature, this could then be referred to an experimentally determined liquidus for the appropriate salt system to calculate a salinity. (Such liquidus for various salt systems have already been extensively determined.

Thus, the ice melting temperature of the samples of irreducible water trapped during formation of three-phase inclusions was able to be used to calculate a salinity for the irreducible water and from this, the resistivity of the reducible water could be determined.

In one test, salinity was estimated from the melting point of ice using the expression:

$$S = (-1.76 T_{ice} - 0.041 T_{ice}^2 - 0.00037 T_{ice}^3) \times 10000 \qquad (1)$$

which was modified after a regression on the NaCl—$H_2O$ system to give approximate agreement with the $CaCl_2$—$H_2O$ system at melting points below $-21°$ C. In the equation (1), the salinity is represented as S and $T_{ice}$ is the final melting temperature of the aqueous phase in the three-phase inclusion.

In a first experiment:

$$T_{ice} = -4.5° \text{ C.}$$

and $$S = (-1.76(-4.5) - 0.041(-4.5)^2 - 0.00037(-4.5)^3) \times 10000$$

i.e.

$$S = 71{,}200 \text{ ppm}$$

Resistivity Rw was then calculated. Rw is dependent on the temperature of the reservoir and was calculated from salinity using the expression:

$$Rw_{FT} = 2330.9 \times (S^{-0.8995}) \times \frac{82}{1.8 \times FT(° \text{C.}) + 39} \qquad (2)$$

which is modified from the Arps formula, where FT is the formation (or reservoir) temperature. Formation temperature is the temperature of the reservoir and depends on the thermal conductivity of the sediments and the geothermal gradient. It is usually measured by a thermometer instrument down the hole. An average geothermal gradient in a sedimentary basin is about 30° C. increase in temperature per kilometer increase in depth.

In the first experiment:

$$Rw_{FT} = 2330.9 \times (71200^{-0.8995}) \times \frac{82}{1.8 \times FT(° \text{C.}) + 39}$$

i.e.: $Rw_{60° \text{ C.}} = 0.06 \Omega m$

Oil Reserves Estimation

Once Rw was calculated, water saturation (Sw) and thence oil saturation (So) of the reservoir was determined using the Archie equation for clean sandstone. Specifically, Sw and So were calculated according to the following equations:

$$Sw = \left( \frac{a}{\phi^m} \times \frac{Rw}{Rt} \right)^{\frac{1}{n}} \qquad (3)$$

$$So = 1 - Sw \qquad (4)$$

where
  Sw=water saturation of uninvaded zone,
  So=oil saturation
  Rw=resistivity of formation water calculated in formula (2),
  Rt=true resistivity of the formation (ie. corrected for invasion),
  $\phi$=the porosity,
  a=the tortuosity factor,
  m=cementation exponent, and
  n=saturation exponent (which for sandstone varies from 1.8 to 2.5 but is normally equal to 2.0).

In the first experiment:

$$Sw = \left( \frac{0.56}{0.17^{1.96}} \frac{0.06}{100} \right)^{\frac{1}{1.85}}$$

$$Sw = 0.08$$

$$So = 1 - 0.08$$

$$So = 0.92$$

where
  Sw=water saturation of the uninvaded zone=0.08
  So=oil saturation=0.92
  Rw=resistivity of formation water at formation temperature=0.06 $\Omega$m
  Rt=true resistivity of formation (i.e. corrected for invasion)=100 $\Omega$m
  $\phi$=porosity=17%
  a=tortuosity factor=0.56
  m=cementation exponent=1.96
  n=saturation exponent=1.85

So was then used for calculating volumetric producible hydrocarbon reserves according to the following equation:

$$N_r = \frac{7758 \times DA \times H \times \phi So \times RF}{BOI} \qquad (5)$$

The effect of salinity changes was observed to range from moderate to dramatic depending on the level of salinity over which the changes took place (see FIG. 1).

In the first experiment:

$$N_r = \frac{7758 \times 500 \times 308 \times 0.17 \times 0.91 \times 0.5}{1.55}$$

$$N_r = 59.62 \text{ million } STB$$

where
  Nr=volumetric recoverable oil reserves in stock tank barrels (STB)=59.62
  DA=drainage area in acres=500 h=reservoir thickness in feet=308

ϕ=porosity=17% (used in the equation as a fraction, i.e. 0.17)

So=oil saturation (1.0−Sw)=0.92

RF=recovery factor=0.5

BOI=oil volume factor or reservoir barrels per stock tank barrel=1.55

GOR=gas oil ratio=100 where $$BOI = 1.05 + 0.5 \times \left(\frac{100}{100}\right)$$

$$BOI = 1.55$$

$$GOR = \frac{100}{1}$$

$$GOR = 100$$

FIG. 1 is a graphical representation of how changing resistivity effects reserves calculations. Electrical resistance of water and aqueous solution depends on the current carrying ions rather than the water medium. A given value of electrical resistance results from a quantity of current carrying ions, thus as the salinity increases the amount of solution required to provide the quantity of current carrying ions decreases. Consequently, as salinity increases and Rw decreases, the amount of solution determined to be present for a given resistivity in the formation decreases; i.e. the calculated Sw decreases, and So (given by Sw=1−So) increases (ie. oil reserves estimation increases).

Example 2

Resistivities of 0.06 to 0.05 Ωm were determined from ice melting temperatures on the aqueous fraction of three-phase inclusions in samples from the Toro and Imburu Formations as part of a major investigation of groundwater and hydrocarbon migration in the Papuan Basin, Papua New Guinea.

Present day resistivities in the Toro and Imburu Formations are about 0.34 to 0.29 Ωm indicating that oil charge occurred before the present day hydrologic system was emplaced. This change in resistivity of palaeoformation waters is part of a larger change in resistivity from waters of 0.017 Ωm at palaeotemperatures of 40 to 50° C. to 0.34 to 0.29 Ωm at present day.

The decrease in Sw resulting from the use of lower resistivities for the irreducible water in the oil zone yielded a corresponding increase in So and in the oil volume calculated to be in the reservoir.

Keeping other factors constant and changing Sw during reserves calculation, resulted in significant changes in calculated oil volumes. For example, using the Sw calculated from three-phase fluid inclusion resistivity data compared with the Sw calculated from present day formation water resulted in an estimated 25% increase in reserves for fields studied in the Papuan Foldbelt. In other words, the present day formation water was not indicative of the actual irreducible water (as originally charged) in the reservoir.

Figure 2:
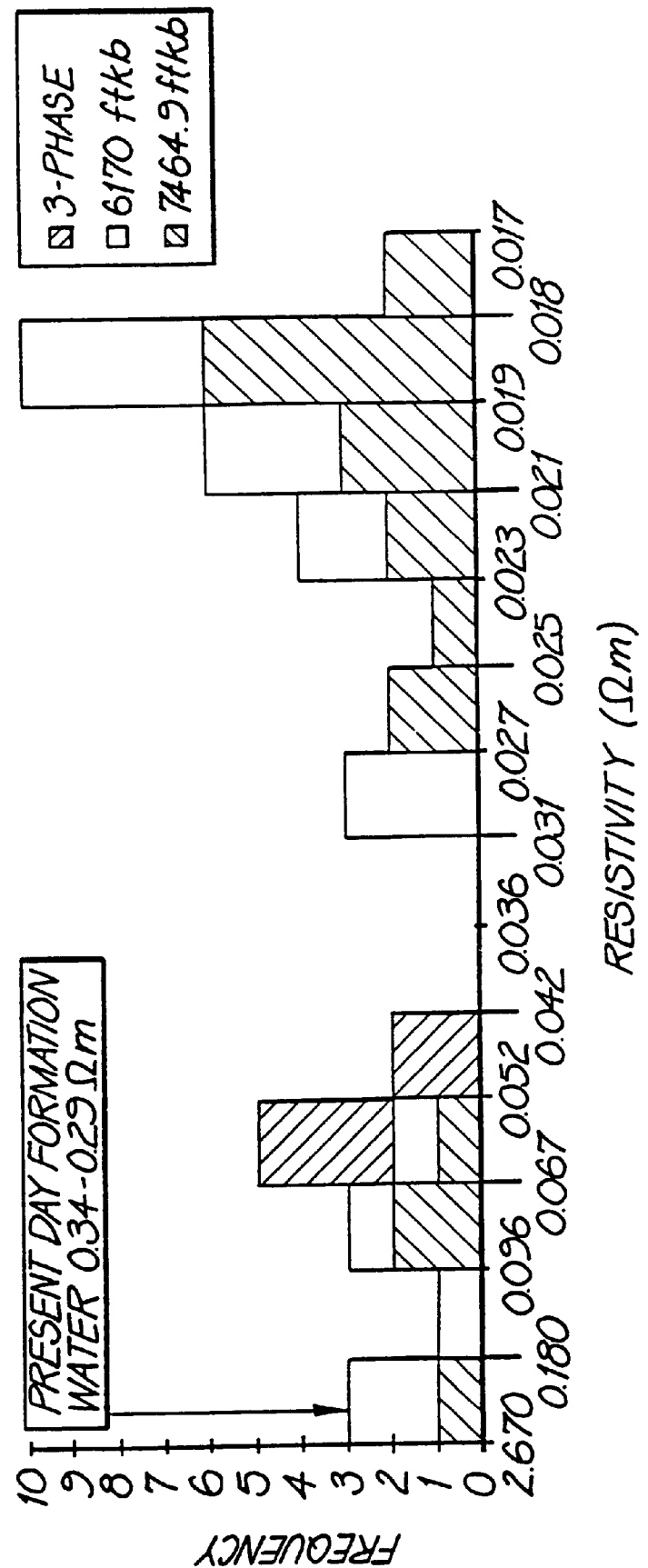
FIG. 2 plots the resistivity data for an oil well in the Papuan Basin.

The results are summarised in FIG. 2 which plots resistivity data for an oil well in the Papuan Basin. The plot shows how resistivity has changed through time from initially low resistivities during the crystallisation of quartz overgrowths to high resistivities at the present day. Superimposed on this are resistivities from 3-phase inclusions. This clearly illustrates that resistivities from 3-phase inclusions, formed during oil accumulation, are lower than those of the present day aquifiers.

Whilst the invention has been described with reference to a number of preferred embodiments, it should be appreciated that the invention can be embodied in many other forms.

We claim:

1. A method for determining the resistivity of water in an oil well site that includes rock that is capable of water entrapment, including the steps of:
   (a) retrieving a sample of the rock;
   (b) identifying any entrapped water in the sample, the entrapped water being irreducible water entrapped as intracrystalline or intragranular inclusions in the sample;
   (c) determining the resistivity of the entrapped water.

2. A method as claimed in claim 1, wherein in step (c) the resistivity is determined by firstly determining the salinity of the entrapped water.

3. A method as claimed in claim 2 wherein the salinity is determined by:
   (1) freezing the entrapped water in the sample;
   (2) causing or allowing the frozen water to melt;
   (3) observing the final melting temperature of the water; and
   (4) calculating salinity from the observed final melting temperature.

4. A method as claimed in claim 3 wherein salinity S is determined according to the formula:

$$S = (-1.76 T_{ice} - 0.041 T_{ice}^2 - 0.00037 T_{ice}^3) \times 10000 \quad (1)$$

where $T_{ice}$ is the final melting temperature determined in step (3).

5. A method as claimed in claim 4 wherein resistivity is calculated according to the formula $$Rw_{FT} = 2330.9 \times (S^{-0.8995}) \times \frac{82}{1.8 \times FT(°C.) + 39} \quad (2)$$

where $Rw_{FT}$ is the resistivity of formation water at a formation temperature, S is the salinity calculated in formula (1) and FT is the formation temperature in °C.

6. A method as claimed in claim 1 wherein the entrapped water is entrapped as a 3-phase intracrystalline inclusion comprising oil, water and gas.

7. A method as claimed in claim 1, wherein entrapped water is located by locating entrapped oil, and entrapped oil is identified by irradiating the sample with violet and/or ultraviolet light.

8. A method as claimed in claim 7, wherein the wavelengths of the light are less than 4000 Angstrom.

9. A method as claimed in claim 1 wherein the sample is produced during the drilling of an oil well site and includes rotary core, cuttings, sidewall core or rotary sidewall core samples.

10. A method for estimating oil reserves in an oil well site including the steps:
   (i) determining the entrapped water resistivity in a method as claimed in claim 1;
   (ii) from the entrapped water resistivity determined in step (i) calculating the water saturation of the well site; and
   (iii) from the calculated water saturation of step (ii), calculating the oil saturation of the well site to enable the estimation of site oil reserves to be made.

11. A method as claimed in claim 10 wherein in step (ii) water saturation is calculated according to the formula $$Sw = \left(\frac{a}{\phi^m} \times \frac{Rw}{Rt}\right)^{\frac{1}{n}} \quad (3)$$

where

Sw=water saturation of uninvaded zone,

Rw=resistivity of formation water calculated in formula (2),

Rt=true resistivity of the formation,

φ=the porosity, a=the tortuosity factor, m=cementation exponent, and n=saturation exponent.

12. A method as claimed in claim 11 wherein in step (iii) oil saturation is calculated according to the formula:

$$So = 1 - Sw \quad (4)$$

where

So=oil saturation and Sw is the water saturation calculated from formula (3); and oil well reserves are then estimated according to the formula:

$$N_r = \frac{7758 \times DA \times h \times \phi \times So \times RF}{BOI} \quad (5)$$

where $N_r$=volumetric recoverable oil reserves in stock tank barrels (STE),

DA=drainage area in acres, h=reservoir thickness in feet,

φ=porosity,

So=oil saturation (i.e. 1.0−Sw),

RF=recovery factor,

BOI=oil volume factor or reservoir barrels per stock tank barrel, and

GOR=gas oil ratio;

where $$BOI = 1.05 + 0.5 \times \left(\frac{GOR}{100}\right) \quad (6)$$

and $$GOR = \frac{\text{gas in cubic feet}}{\text{oil in barrels}}. \quad (7)$$

* * * * *